US012521519B2

(12) United States Patent
Zhan

(10) Patent No.: US 12,521,519 B2
(45) Date of Patent: Jan. 13, 2026

(54) NEGATIVE ION GENERATOR

(71) Applicant: TAIAN BIO-CELL TEC CO., LTD., Taipei (TW)

(72) Inventor: Kun-Quan Zhan, Taipei (TW)

(73) Assignee: TAIAN BIO-CELL TEC CO. , LTD., Taipei (TW)

(*) Notice: Subject to any disclaimer, the term of this patent is extended or adjusted under 35 U.S.C. 154(b) by 286 days.

(21) Appl. No.: 18/462,387

(22) Filed: Sep. 6, 2023

(65) Prior Publication Data

US 2025/0073418 A1 Mar. 6, 2025

(51) Int. Cl.
*A61M 21/02* (2006.01)

(52) U.S. Cl.
CPC .................................. *A61M 21/02* (2013.01)

(58) Field of Classification Search
CPC .................................................... A61M 21/02
See application file for complete search history.

(56) References Cited

FOREIGN PATENT DOCUMENTS

| | | | |
|---|---|---|---|
| DE | 4029860 A1 * | 8/1991 | |
| EP | 1213949 A1 * | 6/2002 | |

OTHER PUBLICATIONS

English Machine Translation of DE 4029860 A1 (Year: 1991).*

* cited by examiner

*Primary Examiner* — Charles S Bushey
(74) *Attorney, Agent, or Firm* — Leong C. Lei

(57) ABSTRACT

The negative ion generator includes an air spray unit, a water reservoir unit, an oscillation illumination assembly, an outer cylinder, and an air blower unit. A dual-nozzle assembly on the air spray unit is designed with a rotary knob mechanism, providing both a vertical and an oblique channel so that users can choose between a direct or oblique spray of the mist. A high-magnetic energy ring within the air spray unit can highly magnetize the passing water molecules and reorganize them to achieve an enhancement effect. A soft water cup of the water reservoir unit employs a hook-on design, allowing users to easily replace the soft water cup and choose different essence flavors. A highly durable material is used for an outer cylinder of the negative ion generator, allowing for customizable printing of distinct patterns. This also reduces the substantial costs required for repairing or replacing ceramic casings.

3 Claims, 10 Drawing Sheets

NEGATIVE ION GENERATOR

BACKGROUND OF THE INVENTION

(a) Technical Field of the Invention

The present invention is generally related to negative ion generators, and more particular to a negative ion generator of improved structure.

(b) Description of the Prior Art

Aromatherapy has been extensively covered in the media regarding its history and application development. While these reports remain somewhat reserved about whether aromatherapy can replace conventional medical treatments, they still provide many optimistic and positive assessments. Moreover, regardless of whether it can genuinely generate widespread therapeutic effects on the human body, as long as a pleasant indoor environment that can soothe the mind is established, people will alleviate discomfort and handle pressures more easily. This can enhance people's emotional management, leading to numerous benefits.

Traditionally, there are several methods for diffusing essential oils into the air, including the heating method (candle/incense warmer, electric diffuser), isopropanol diffusing method, and oxygen-containing diffusing method. However, these methods are generally not recommended by experts due to various factors such as the risk of overheating and combustion, the production of large aromatic molecules that don't disperse well, and the generation of ozone that is harmful to the environment.

Recently, a method that utilizes electrical power to generate high-frequency vibrations for rapidly oscillating and atomizing the mixture of essential oils and carrier liquids has been developed. This ultrasonic aromatherapy method creates a fine mist without the risks associated with heating. It's considered the most effective way to disperse essential oils by accelerating their breakdown into smaller particles. Especially noteworthy is the production of negative ions using ultrasonic aromatherapy, which has gained widespread acceptance for its beneficial effects. This method finds extensive application in households and public spaces.

As shown in FIGS. 1, 2, and 3, a conventional negative ion generator primarily consists of a nozzle rectification assembly 100, an oscillation assembly 200, and an air supply assembly 500. The nozzle rectification assembly 100 is composed of either a direct nozzle 101A or a slanted nozzle 101B, an energy pathway 102, and a rectification unit 103. The oscillation assembly 200 includes an oscillation unit 201, an inner cylinder 202, and a water cup 203. The air supply assembly 500 is a fan 501 secured to a permeable disk 502. There is a middle cylinder 300, its opening slightly flaring like a trumpet, with L-shaped screw sockets 301 at its inner bottom, featuring 4 upper screw holes 302 and 4 lower screw holes 303. The oscillation assembly 200 can be fastened within it using screws 304. A ceramic casing 400, with an opening similarly flaring, fits snugly into the middle cylinder 300. A cast iron base stand 600 is equipped with ventilation holes 601 and screw holes 602. Using screws 603, the relevant components, including the middle cylinder 300, ceramic casing 400, and air supply assembly 500, are fastened together.

The above-mentioned conventional negative ion generators have several drawbacks that could be improved, summarized as follows.

Conventional negative ion generators often utilize ceramic for their outer casings. While ceramic finishes do have their stylistic appeal, acquiring high-quality ceramic clay in recent years has become challenging. The production process for these ceramic casings also involves significant labor and time costs due to the difficulties in obtaining quality clay and the high rate of defects during the creation of raw ceramic forms. Additionally, the hand-painted glazing requires experienced artisans and is highly reliant on manual work. The final products are also vulnerable to damage during assembly, transportation, and use. The fragility of ceramic components leads to an elevated rate of returns for repairs and increased consumption of ceramic materials, resulting in substantial business expenses and human resource investment.

Furthermore, it is commonly observed that negative ion generators use cast iron for their base and stand. However, due to the gradual decline of the casting industry in recent years and the consequent increase in raw material costs, many factories have transitioned to precision machining and manufacturing. The shortage of factories and labor in the casting industry has also added pressure to the cost of casting products. Additionally, the transportation costs for the assembled products have been continuously rising, which becomes a significant obstacle to the promotion of the product.

Moreover, the commonly used nozzle design includes two types: direct spraying and oblique spraying. Users are required to frequently change nozzles according to their usage needs, and the nozzles are also prone to falling off due to accidental collisions. Apart from the high production costs, this design also results in extreme inconvenience during usage.

SUMMARY OF THE INVENTION

Therefore, a novel negative ion generator is provided herein. The negative ion generator includes an air spray unit, a water reservoir unit, an oscillation illumination assembly, an outer cylinder, and an air blower unit.

A major objective of the present invention is to use a highly durable material for the outer cylinder of the negative ion generator, allowing for customizable printing of distinct graphical patterns by transfer printing, painting, or laser engraving. This imparts a youthful and personalized appearance to the negative ion generator. Apart from enhancing the durability of the negative ion generator, this approach also reduces the substantial costs and human resources required for repairing or replacing ceramic casings due to damage. As a result, it achieves the dual purpose of improving quality and reducing expenses and wear.

Another objective of the present invention is that a dual-nozzle assembly on the air spray unit is designed with a rotary knob mechanism, providing both a vertical and an oblique channel. Through rotation, users can choose between a direct or oblique spray of the mist. This intricate design enhances user-friendliness, providing a more humane operation.

Yet another objective of the present invention is to incorporate a high-magnetic energy ring within the air spray unit that is made by a stamping process, rather than the conventional complex casting. This high-magnetic energy ring includes a high-magnetic energy rare earth ring, which can highly magnetize the passing water molecules and reorganize them to achieve an enhancement effect.

Furthermore, a soft water cup of the water reservoir unit employs a hook-on design, allowing users to easily replace the soft water cup and choose different essence flavors.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
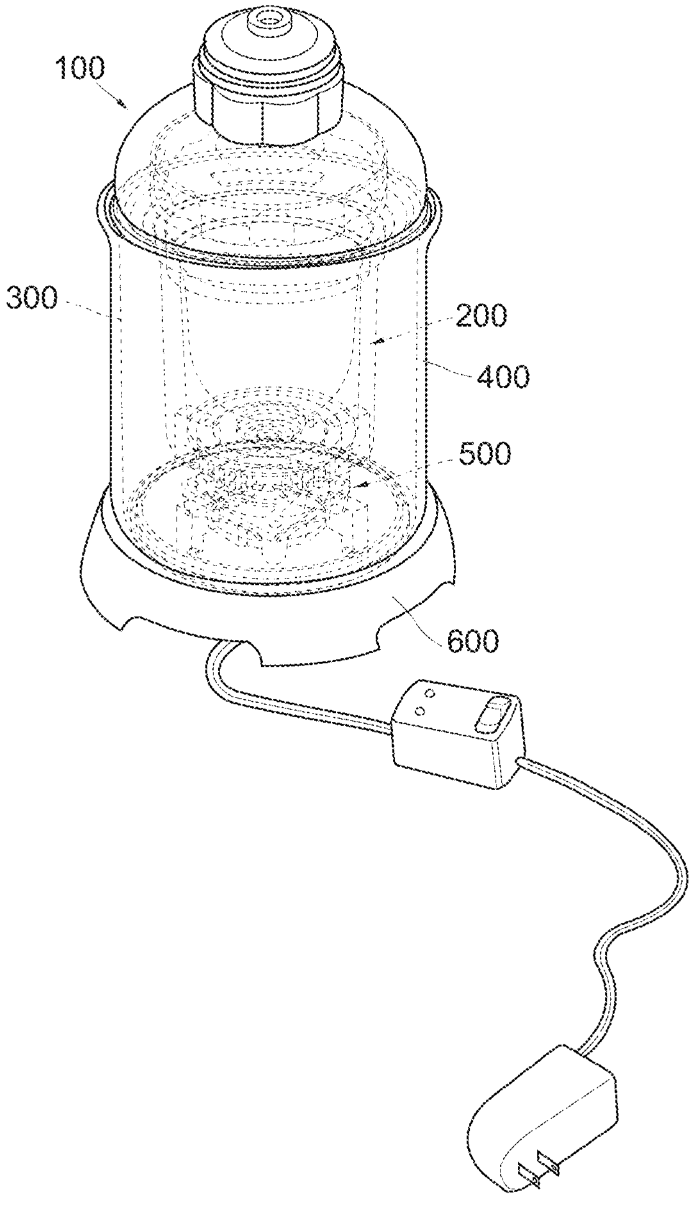
PRIOR ART FIG. 1
FIG. 1 is a perspective diagram showing a conventional negative ion generator.
Figure 2:
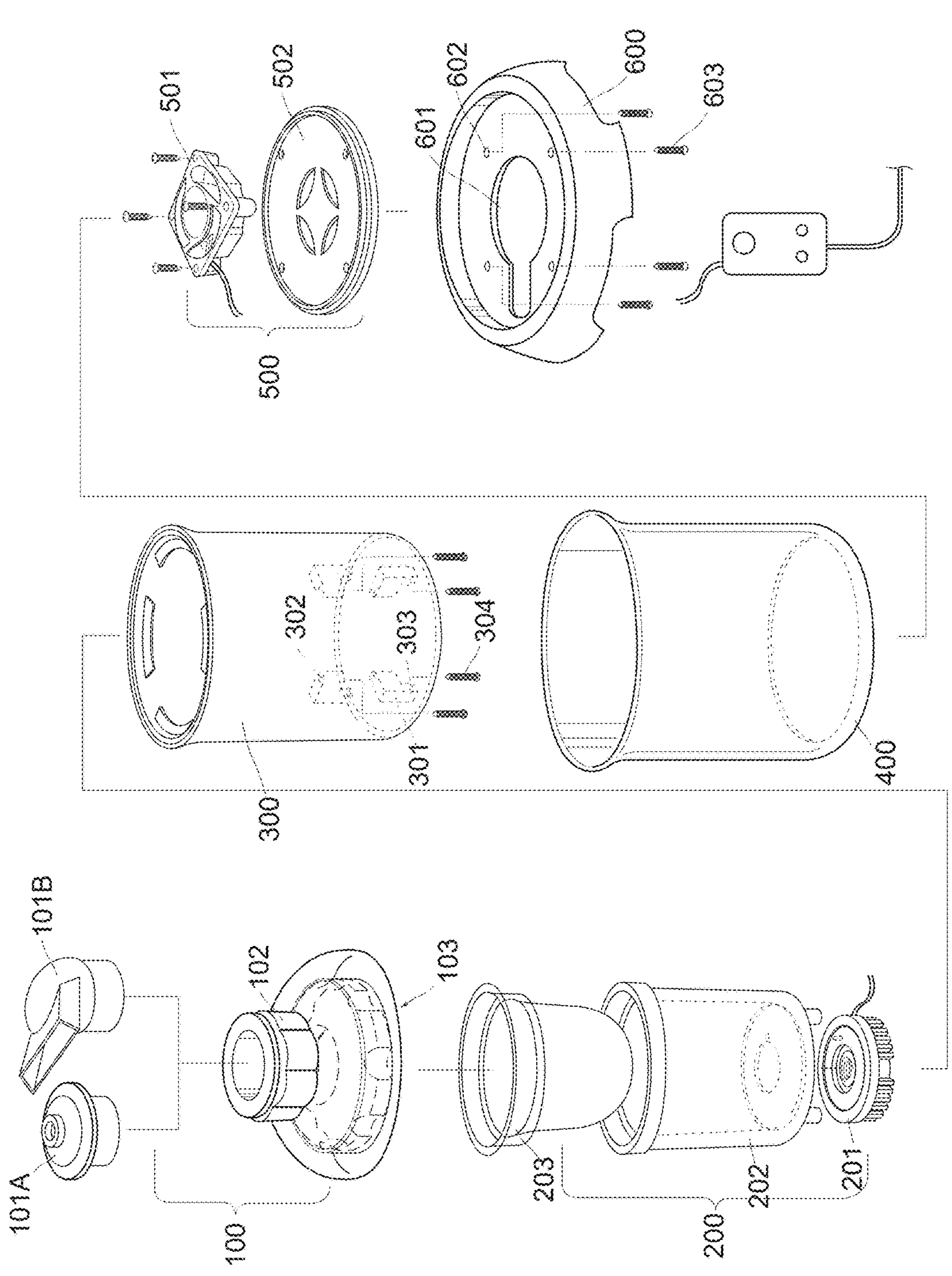
PRIOR ART FIG. 2
FIG. 2 is a perspective breakdown diagram showing the conventional negative ion generator of FIG. 1.
Figure 3:
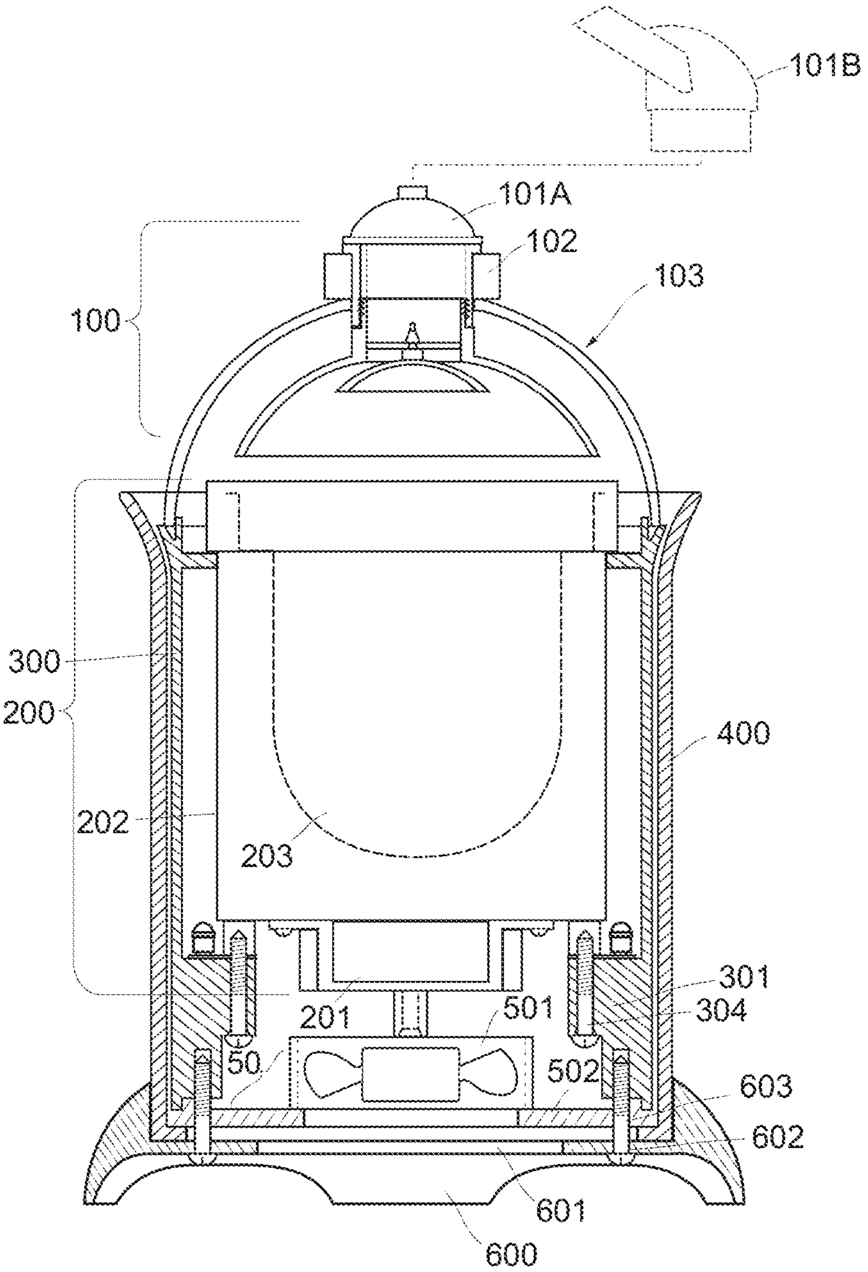
PRIOR ART FIG. 3
FIG. 3 is a sectional diagram showing the conventional negative ion generator of FIG. 1.
Figure 4B:
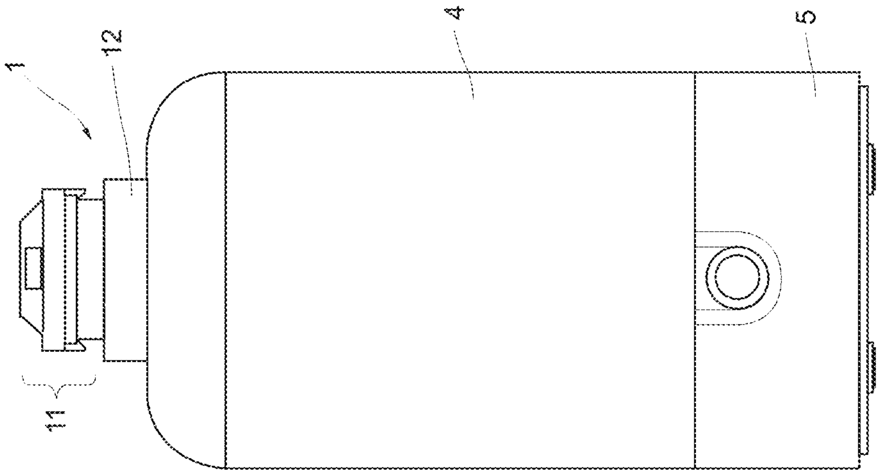
FIGS. 4A and 4B are perspective and profile diagrams of a negative ion generator according to an embodiment of the present invention.
Figure 4A:
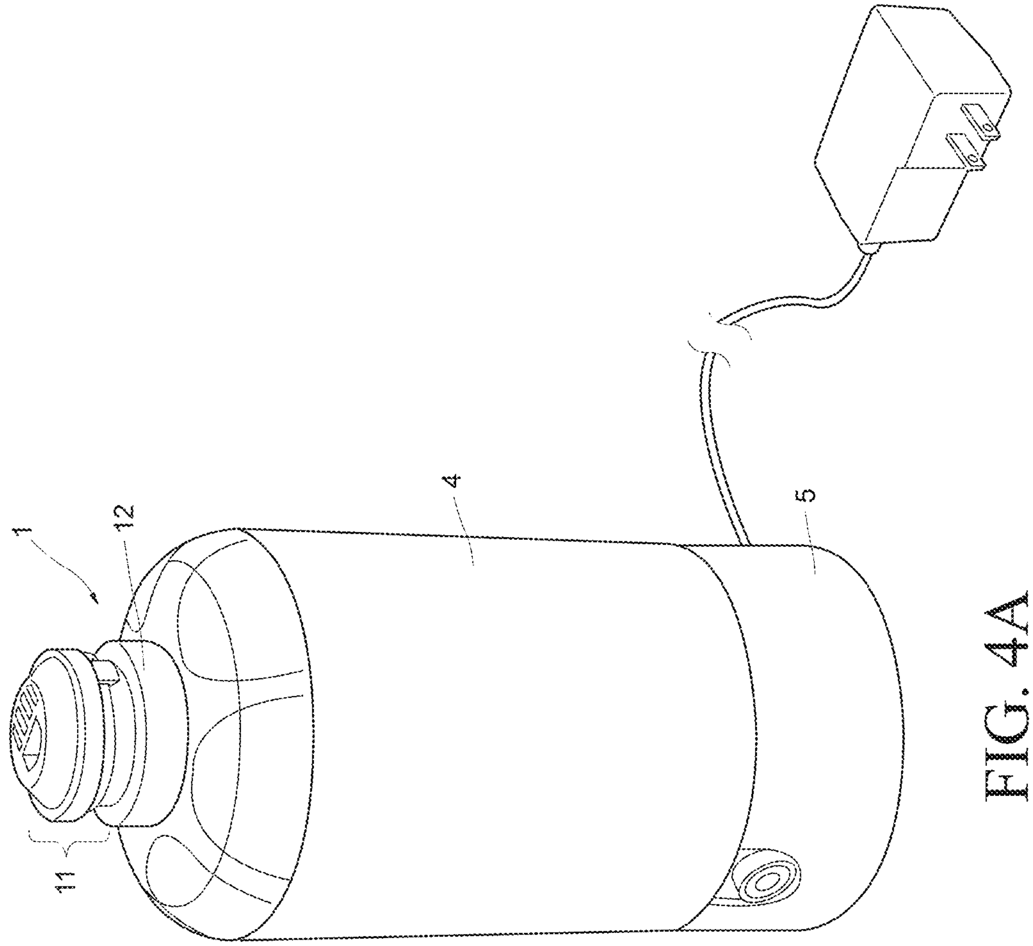
Figure 5:
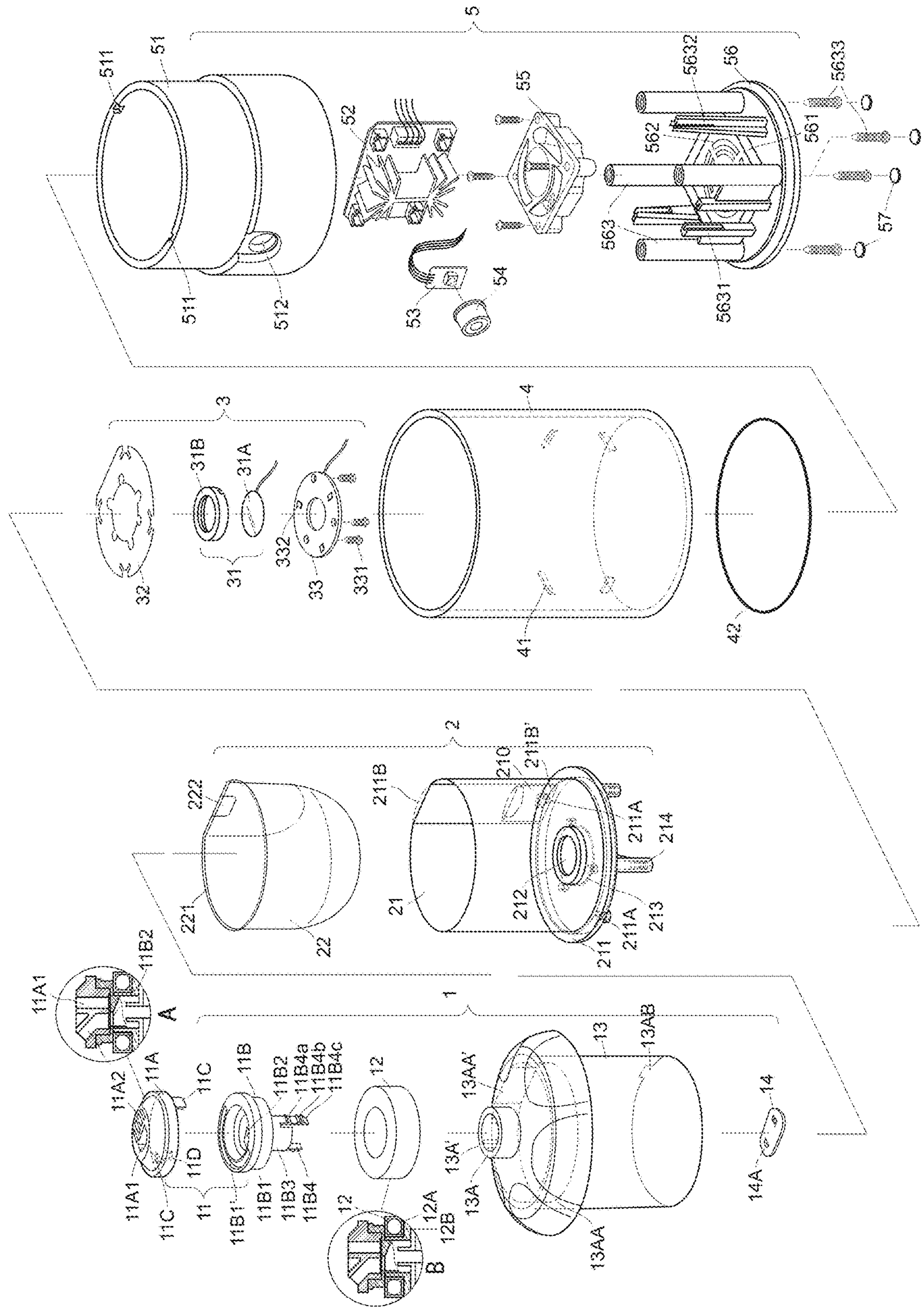
FIG. 5 is a perspective breakdown diagram showing the negative ion generator of FIGS. 4A and 4B.

As shown in FIGS. 4A, 4B, and 5, a negative ion generator according to an embodiment of the present invention includes an air spray unit 1, a water reservoir unit 2, an oscillation illumination assembly 3, an outer cylinder 4, and an air blower unit 5. The air spray unit 1 includes a dual-nozzle assembly 11, a high-magnetic energy ring 12, an air spray cylinder 13, and a guiding piece 14. As shown in the circle A of FIG. 5, the dual-nozzle assembly 11 is designed with a rotary knob, consisting of an upper rotary knob 11A and a lower nozzle base 11B. The upper rotary knob 11A provides both a vertical channel 11A1 and an oblique channel 11A2, with a hook 11C protruding downward on its sides. Positioned just below a front edge of the upper rotary knob 11A is a tenon 11D. The lower nozzle base 11B is cup-shaped and includes a ring-shaped flange 11B1 on its upper part, a semi-circle through hole 11B2 is set on its lower part, a tubular body 11B3 extending downward from the lower part, and two two-stage hooks 11B4. Each two-stage hook 11B4 includes a main hook body 11B4*a*, a guiding-piece stopper 11B4*b*, and a guiding-piece hook 11B4*c* arranged from top to bottom. On the ring-shaped flange 11B1 of the lower nozzle base 11B, there is a 180° semi-circle groove 11B1'. Thus, the upper rotary knob 11A and the lower nozzle base 11B can be pressed and interlocked together. The hook 11C can conveniently engage the ring-shaped flange 11B1, and the tenon 11D can fit into the semi-circle groove 11B1'. The upper rotary knob 11A can only be turned within a 180° rotational range. Users can easily choose between the vertical channel 11A1 and the oblique channel 11A2 to generate either direct spraying or oblique spraying of mist.

The air spray cylinder 13 is a columnar case with an umbrella-shaped top. It is equipped with a positioning groove 13AB at the rear lower part. An annular collecting short wall 13AA is set beneath the umbrella-shaped top. The rear part of this short wall forms a flat cut surface 13AA', serving as an air passage inlet. A hollow columnar body 13A, which passes through the center, is prominently positioned at the upper end. The inner edge of the columnar body 13A is equipped with guide rails 13A', which allow for the insertion of the high-magnetic energy ring 12 and the secure locking of the dual-nozzle assembly 11. The guiding piece 14 is a long elliptical-shaped thin piece with two corresponding elongated holes 14A. To assemble of the air spray unit 1, the high-magnetic energy ring 12 is first inserted and locked into place, followed by the insertion and securing of the dual-nozzle assembly 11. The two-stage hooks 11B4 descend along the guide rails 13A', and the main hook body 11B4*a* can fit snugly into the bottom edge of the hollow columnar body 13A. The guiding-piece stopper 11B4*b* and guiding-piece hook 11B4*c* run through the elongated holes 14A of the guiding piece 14 so that the guiding piece 14 is securely locked in place between the guiding-piece stopper 11B4*b* and guiding-piece hook 11B4*c* without the risk of falling out.

As shown in the circle B of FIG. 5, the high-magnetic energy ring 12 employs a stamping manufacturing process, instead of the conventional complex casting process, to take the form of a circular body housing a high-magnetic energy rare earth ring 12A encapsulated in a ring piece 12B. This configuration highly magnetizes passing water molecules, causing them to become finer and rearranged, resulting in the characteristic effect of enhancing negative ion generation.

The water reservoir unit 2 is composed of a main water cup 21 and a soft water cup 22. The main water cup 21 is a cylindrical body with a positioning protrusion 210 set on the lower rear edge. The bottom of the main water cup 21 protrudes outward with a ring-shaped flange 211, and there are positioning tabs 211A placed at intervals beneath the ring-shaped flange 211. These tabs can conveniently interlock with the positioning recesses 511 on the air blower tube 51. The rear part of the main water cup 21 features a flat area that, when the main water cup 21 is inserted into the cylinder of the air spray unit 1, forms a curved petal-like air passage 211B. A corresponding air hole 211B' is provided beneath the air passage 211B to allow for air flow. Below the central through hole 212, an annular cylindrical chamber 213 is placed to accommodate the insertion of the oscillation unit

31. The oscillation unit 31 includes an oscillation plate 31A and a silicon seat 31B. The oscillation illumination assembly 3 is formed as follows. First, the shielding piece 32 is attached, followed by securing the luminescent pressure plate 33 with screws 331. The luminescent pressure plate 33 is equipped with LED light elements 332. Additionally, the main water cup 21 has four threaded columns 214 downwardly extended, serving for assembly purposes.

The soft water cup 22 is designed to match the shape of the main water cup 21. It has a locking rim 221 around its top opening, and a hanging tab 222 protruding from a rear flat area. When placed inside the main water cup 21, the hanging tab 222 hangs on the flat edge of the main water cup 21's rear flat area.

The outer cylinder 4 is a hollow cylindrical body with a top opening and a bottom opening. Around its inner wall's lower half, there are four inverted hook tabs 41 and a tightening ring 42, serving to tighten the outer cylinder.

The air blower unit 5 is composed of the air blower tube 51 that is vertically hollow and resembles the shape of a cake tower, a main control board 52, a switch circuit board 53, a button 54, a fan 55, and a base 56. The air blower tube 51 has positioning recesses 511 on its upper rim, which perfectly align with the positioning tabs 211A of the ring-shaped flange 211. A button hole 512 is placed on the air blower tube 51 for the button 54. The main control board 52 is responsible for related electronic control, and includes oscillation circuit, illumination circuit, fan circuit, voltage conversion circuit, etc. The main control board 52 interfaces with the switch circuit board 53. By pressing the button 512, functions such as start, light off, timing, and power interruption can be configured. The voltage conversion circuit offers the choice of using indoor power or portable power sources.

The base 56 is a disk-shaped structure with a square fan chamber 561 in the center and an air inlet 562. Threaded columns 563 are positioned at four corners, and between two front threaded columns 563, there's a seat 5631 for installing the switch circuit board 53. Between the front and rear threaded columns 563, there is another seat 5632 for installing the main control board 52. By using assembly screws 5633, the water reservoir unit 2 and the air blower unit 5 are securely attached to form a single unit. The tightening ring 42 is placed on the air blower tube 51, and then the air blower tube 51 is fitted into the outer cylinder 4. The four inverted hook tabs 41 inside the outer cylinder 4 firmly secure it to the ring-shaped flange 211 of the main water cup 21. Four anti-slip foot pads 57 are attached to the bottom of the base 56, enhancing the stability and shock absorption of the negative ion generator. By following these steps, the optimized structure of the negative ion generator is assembled.

Figure 6B:
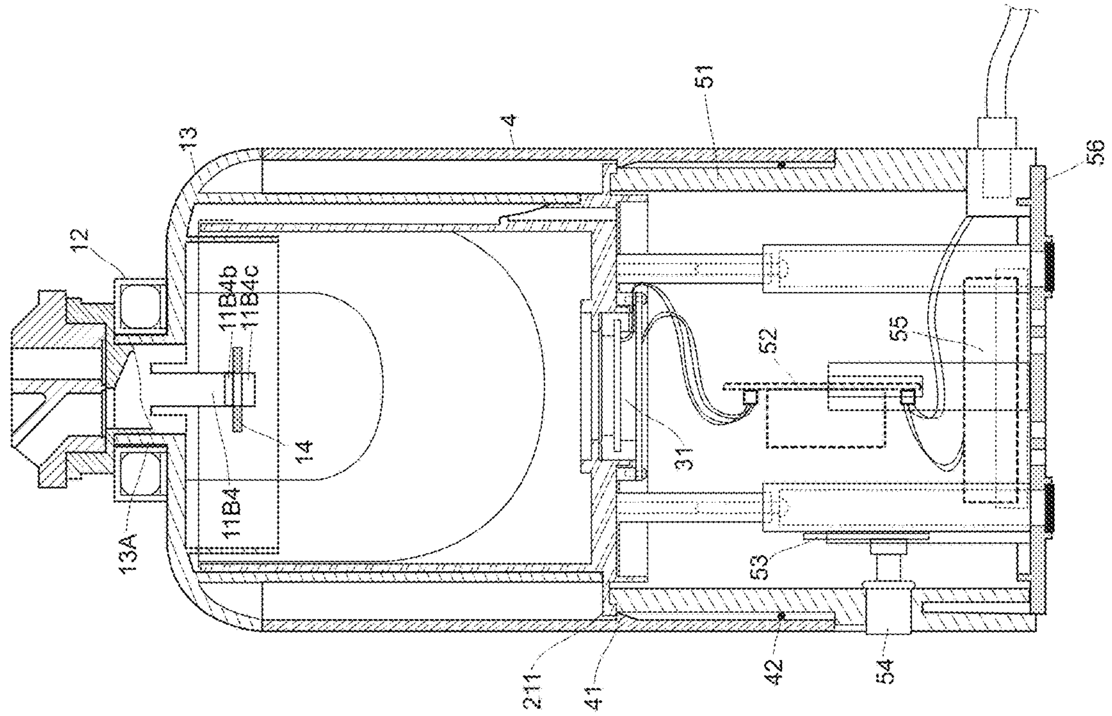
FIGS. 6A and 6B are sectional diagrams of the negative ion generator of FIGS. 4A and 4B.
Figure 6A:
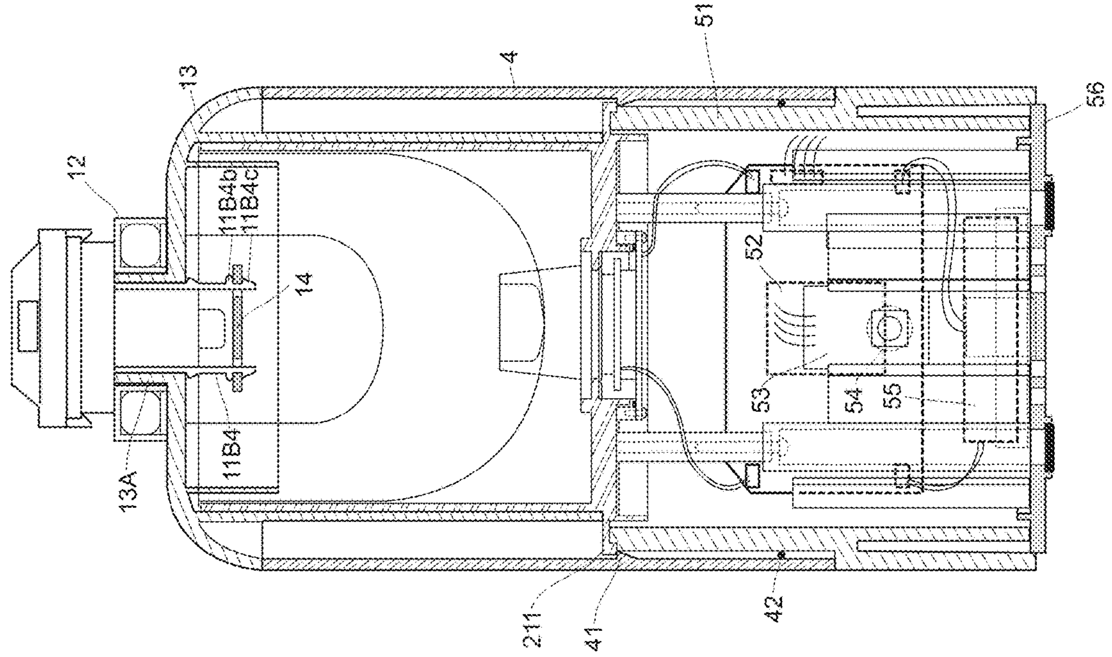

As shown in FIGS. 6A and 6B, to assemble the negative ion generator of the present invention, the high-magnetic energy ring 12 is first placed onto the hollow columnar body 13A at the upper part of the air spray cylinder 13. Then, the dual-nozzle assembly 11 is inserted into the air spray cylinder 13, secured firmly by the two-stage hooks 11B4 that tightly hold the air spray cylinder 13. Next, the guiding piece 14 is positioned between the guiding-piece stoppers 11B4*b* and the guiding-piece hooks 11B4*c* of the two-stage hooks 11B4.

The tightening ring 42 is inserted into the air blower tube 51, and then the air blower tube 51 is threaded into the outer cylinder 4. At this point, the four inverted hook tabs 41 interlock with the ring-shaped flange 211, creating a secure locking effect. Simultaneously, with the tightening ring 42, a tightly sealed assembly is achieved. Other components such as the main control board 52, switch circuit board 53, button 54, and fan 55 are assembled using a combination of interlocking or screwing methods. Finally, the air blower tube 51 is integrated with the base 56 using assembly screws 5633.

Figure 7:
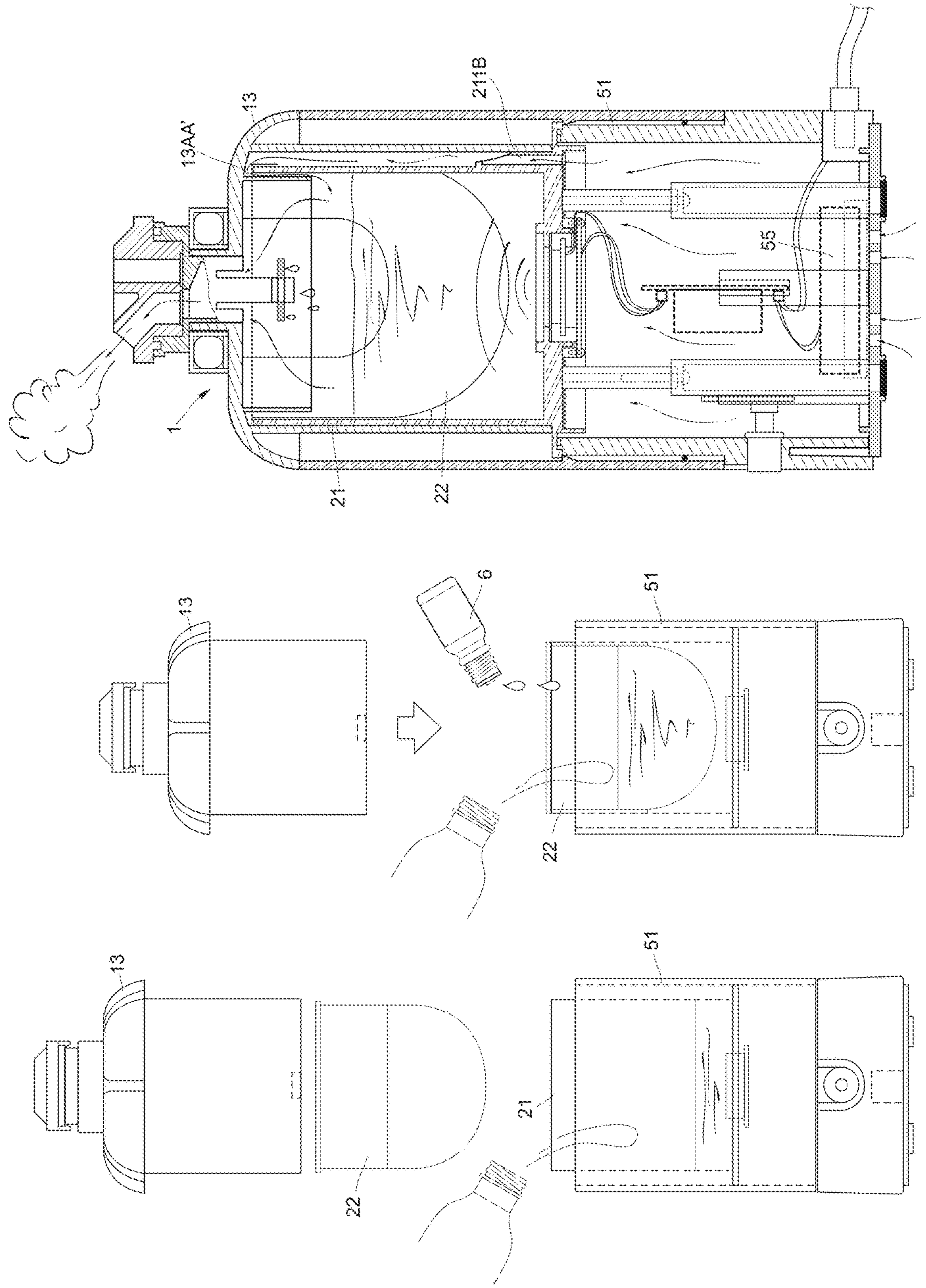
FIG. 7 shows a usage scenario of the negative ion generator of FIGS. 4A and 4B.

As shown in FIG. 7, to operate the negative ion generator of the present invention, distilled water is first poured into the main water cup 21 to a depth of about 1 centimeter. Then, the soft water cup 22 is placed inside and fill it with distilled water to about half its height. Depending on user preference, different types of essence or extracts 6 can be added into the soft water cup 22. The air spray cylinder 13 is placed, and the negative ion generator is activated to initiate the generation process. The fan 55 draws air in, guiding it through the air blower tube 51. The air within the air blower tube 51 moves upward through the air passage 211B, and then enters the soft water cup 22 through the flat cut surface 13AA' at the upper end of the air spray cylinder 13. The oscillation unit 31 generates high-frequency oscillations in the water. Using distilled water as a conducting medium, these oscillations cause the water molecules to become extremely small and move upwards. The air spray unit 1 then sends out high-oxygen concentration negative ions. To ensure smooth operation, the guiding piece 14 effectively prevents water droplets from causing turbulence, allowing the airflow to move smoothly upward.

Figure 8B:
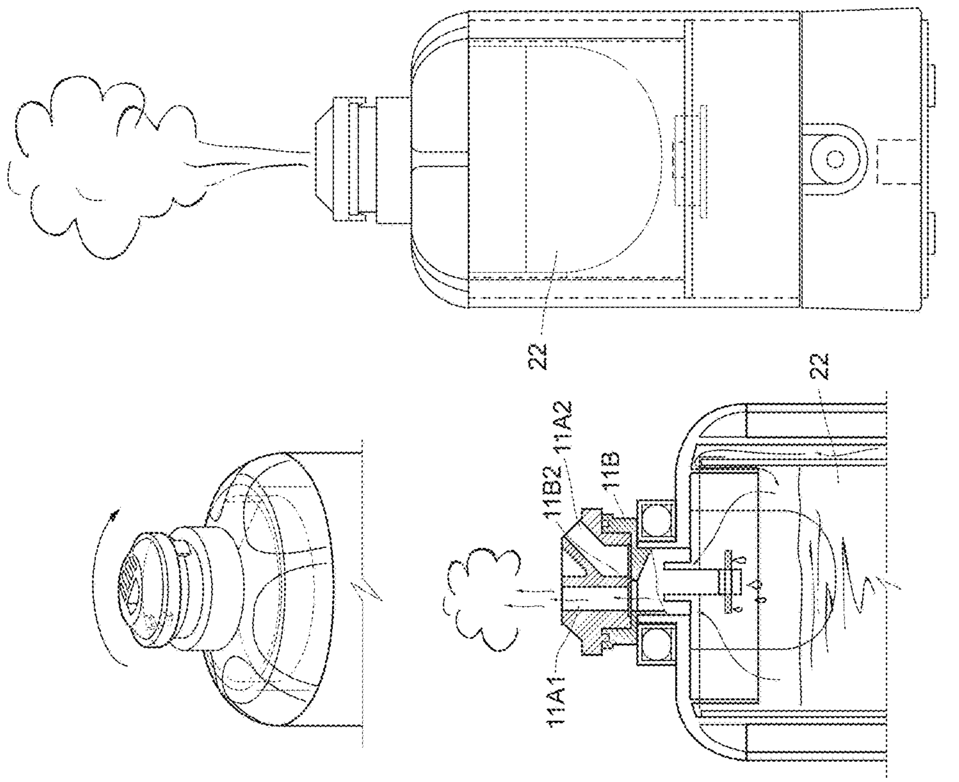
FIGS. 8A and 8B shows usage scenarios of a dual-nozzle assembly of the negative ion generator of FIGS. 4A and 4B.
Figure 8A:
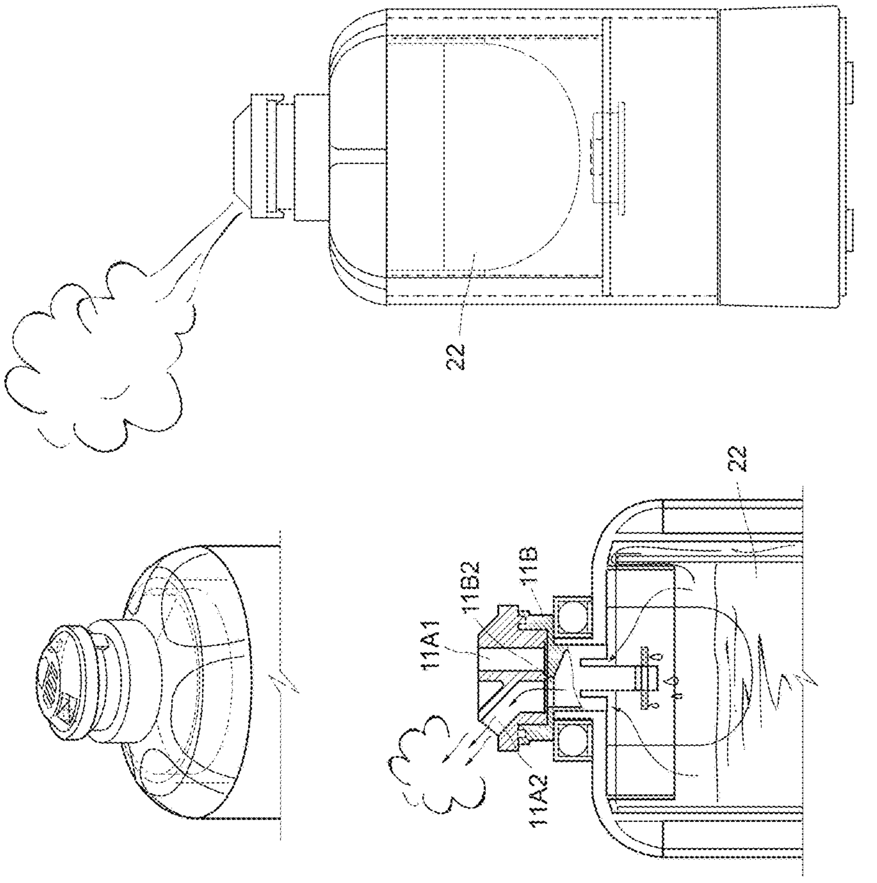

FIG. 8A illustrates the negative ion generator operating in the oblique spraying mode. As shown, the negative ionized water vapor from the soft water cup 22 is emitted diagonally through the semi-circle through hole 11B2 on the lower nozzle base 11B. It then travels outward through the oblique channel 11A2, creating an angled spray effect. FIG. 8B depicts the direct spraying mode. As shown, the negative ionized water vapor from the soft water cup 22 is expelled diagonally through the semi-circle through hole 11B2 on the lower nozzle base 11B. Subsequently, it is directed outward through the vertical channel 11A1, producing a direct spray effect.

Figure 9:
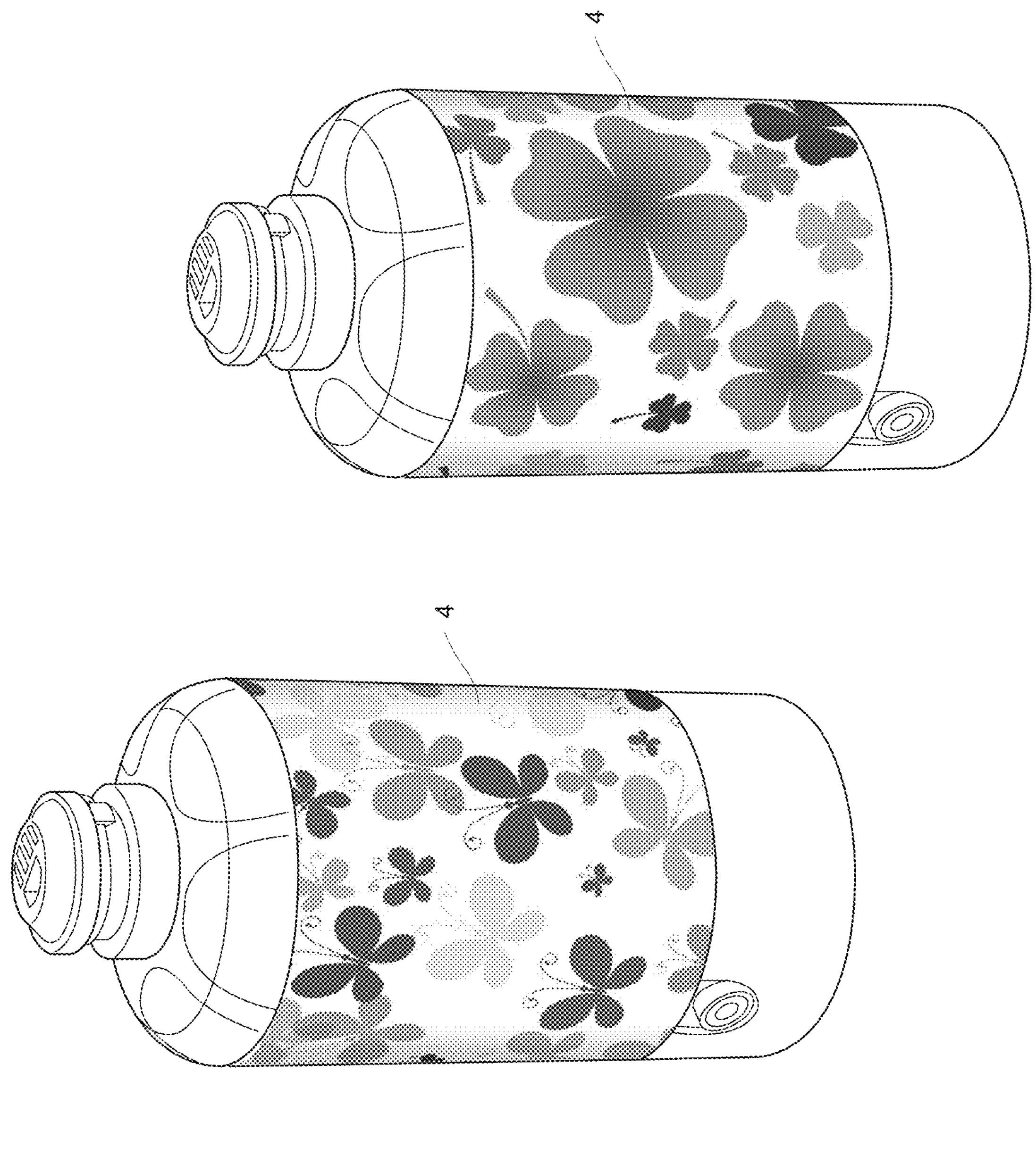
FIG. 9 is a perspective diagram showing an outer cylinder of the negative ion generator of FIGS. 4A and 4B.

As shown in FIG. 9, the outer cylinder 4 can be printed in various colors and patterns according to market demands or specific purposes. This diversity in design meets market needs while also offering lightweight and impact-resistant characteristics, effectively enhancing the negative ion generator's usability.

Figure 10:
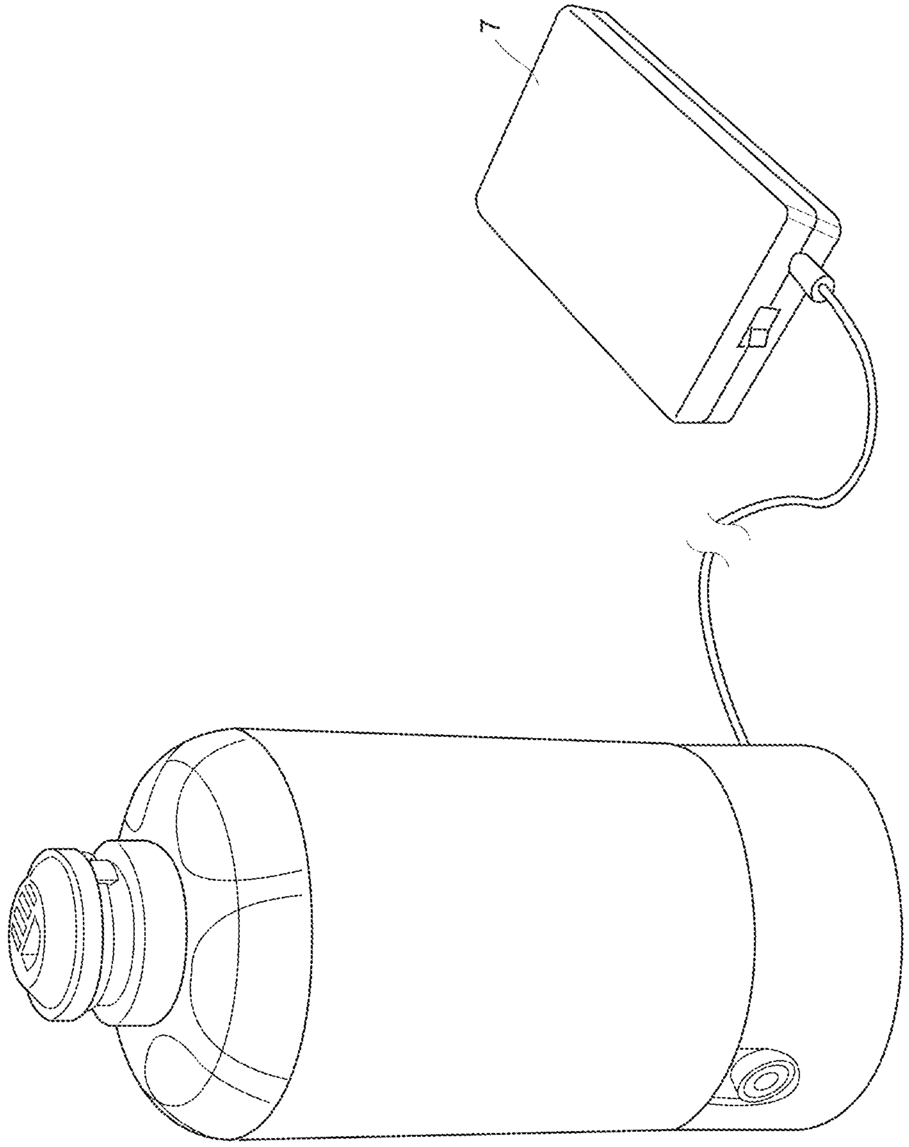
FIG. 10 shows the negative ion generator of FIGS. 4A and 4B operated with a portable charger.

As shown in FIG. 10, the negative ion generator of the present invention adopts a dual-circuit design. Therefore, the negative ion generator not only can be powered by household mains for indoor usage, but also can be powered by a portable charger 7, enabling convenient portability and unrestricted use across different locations.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A negative ion generator, comprising an air spray unit, a water reservoir unit, an oscillation illumination assembly, an outer cylinder, and an air blower unit, wherein the air spray unit comprises a dual-nozzle assembly, a high-magnetic energy ring, an air spray cylinder, and a guiding piece; the dual-nozzle assembly comprises an upper rotary knob and a lower nozzle base; the upper rotary knob provides both a vertical channel and an oblique channel; the upper rotatory knob has a hook protruding downward and a tenon positioned just below a front edge of the upper rotary knob; the lower nozzle base is cup-shaped with a ring-shaped flange on an upper part, a semi-circle through hole set on a lower part, a tubular body extending downward from the lower part, and two two-stage hooks; each two-stage hook comprises a main hook body, a guiding-piece stopper, and a guiding-piece hook arranged from top to bottom; a 180° semi-circle groove is configured on the ring-shaped flange; the upper rotary knob and the lower nozzle base are pressed and interlocked together; the hook engages the ring-shaped flange, and the tenon fits into the semi-circle groove; the upper rotary knob is rotatable within a 180° rotational range;

the air spray cylinder is a columnar case with an umbrella-shaped top equipped with a positioning groove at a rear lower part; an annular collecting short wall is set beneath the umbrella-shaped top; the rear part of this short wall forms a flat cut surface, serving as an air passage inlet; a hollow columnar body, which passes through the center, is prominently positioned at an upper end; an inner edge of the columnar body is equipped with guide rails, which allow for the insertion of the high-magnetic energy ring and the secure locking of the dual-nozzle assembly; the guiding piece is a long elliptical-shaped thin piece with two corresponding elongated holes; to assemble of the air spray unit, the high-magnetic energy ring is inserted and locked into place, followed by the insertion and securing of the dual-nozzle assembly; the two-stage hooks descend along the guide rails, and the main hook body fits snugly into a bottom edge of the hollow columnar body; the guiding-piece stopper and guiding-piece hook run through the elongated holes of the guiding piece so that the guiding piece is securely locked in place between the guiding-piece stopper and guiding-piece hook without the risk of falling out;

the high-magnetic energy ring employs a stamping manufacturing process to take the form of a circular body housing a high-magnetic energy rare earth ring encapsulated in a ring piece; the high-magnetic energy ring highly magnetizes passing water molecules, causing water molecules to become finer and rearranged, resulting in the characteristic effect of enhancing negative ion generation;

the water reservoir unit comprises a main water cup and a soft water cup; the main water cup is a cylindrical body with a positioning protrusion set on a lower rear edge; a bottom of the main water cup protrudes outward with a ring-shaped flange, and there are positioning tabs placed at intervals beneath the ring-shaped flange; these tabs interlock with positioning recesses on the air blower unit; a rear part of the main water cup features a flat area that, when the main water cup is inserted into the air spray unit, forms a curved petal-like air passage; a corresponding air hole is provided beneath the air passage to allow for air flow; below the central through hole, an annular cylindrical chamber is placed; the main water cup has four threaded columns downwardly extended, serving for assembly purposes;

the oscillation illumination assembly comprises an oscillation unit inserted in the annular cylindrical chamber, a shielding piece attached to the oscillation unit, and a luminescent pressure plate equipped with LED light elements; the oscillation unit comprises an oscillation plate and a silicon seat; the luminescent pressure plate is secured with screws;

the soft water cup is designed to match the shape of the main water cup; the soft water cup has a locking rim around a top opening, and a hanging tab protruding from a rear flat area; when placed inside the main water cup, the hanging tab hangs on a flat edge of the main water cup's rear flat area;

the outer cylinder is a hollow cylindrical body with a top opening and a bottom opening; around an inner wall's lower half, there are four inverted hook tabs and a tightening ring, serving to tighten the outer cylinder;

the air blower unit comprises an air blower tube that is vertically hollow and resembles the shape of a cake tower, a main control board, a switch circuit board, a button, a fan, and a base; the air blower tube has positioning recesses on an upper rim, which align with the positioning tabs of the ring-shaped flange; a button hole is placed on the air blower tube for the button;

the base is a disk-shaped structure with a square fan chamber and an air inlet; threaded columns are positioned at four corners; between two front threaded columns, there's a seat for installing the switch circuit board; between front and rear threaded columns, there is another seat for installing the main control board; by using assembly screws, the water reservoir unit and the air blower unit are securely attached to form a single unit; the tightening ring is placed on the air blower tube, and then the air blower tube is fitted into the outer cylinder; the four inverted hook tabs inside the outer cylinder are firmly secured to the ring-shaped flange of the main water cup; and four anti-slip foot pads are attached to the bottom of the base, enhancing stability and shock absorption of the negative ion generator.

2. The negative ion generator according to claim 1, wherein the outer cylinder is printed with a graphical pattern by transfer printing, painting, or laser engraving.

3. The negative ion generator according to claim 1, wherein the main control board interfaces with the switch circuit board and comprises an oscillation circuit, an illumination circuit, a fan circuit, and a voltage conversion circuit, providing start, light off, timing, and power interruption to the negative ion generator; and the voltage conversion circuit offers the choice of using indoor power or a portable power source.

* * * * *